(12) United States Patent
Gross et al.

(10) Patent No.: US 11,344,721 B1
(45) Date of Patent: May 31, 2022

(54) CARTILAGE TREATMENT

(71) Applicant: RAINBOW MEDICAL LTD., Herzliya (IL)

(72) Inventors: Yossi Gross, Moshav Mazor (IL); Yuval Mandelbaum, Gat-Rimon (IL)

(73) Assignee: RAINBOW MEDICAL LTD., Herzliya (IL)

( * ) Notice: Subject to any disclaimer, the term of this patent is extended or adjusted under 35 U.S.C. 154(b) by 0 days.

(21) Appl. No.: 17/402,911

(22) Filed: Aug. 16, 2021

(51) Int. Cl.
*A61N 1/08* (2006.01)
*A61N 1/05* (2006.01)
*A61N 1/32* (2006.01)

(52) U.S. Cl.
CPC ............. *A61N 1/326* (2013.01); *A61N 1/05* (2013.01); *A61N 1/08* (2013.01)

(58) Field of Classification Search
CPC ............. A61N 1/326; A61N 1/05; A61N 1/08
See application file for complete search history.

(56) References Cited

U.S. PATENT DOCUMENTS

| | | | |
|---|---|---|---|
| 4,044,774 A | 8/1977 | Corbin et al. | |
| 4,360,031 A | 11/1982 | White | |
| 4,503,863 A | 3/1985 | Katims | |
| 4,602,638 A * | 7/1986 | Adams | A61N 1/05 607/52 |
| 4,710,174 A | 12/1987 | Moden et al. | |
| 4,738,250 A * | 4/1988 | Fulkerson | A61N 1/326 607/50 |
| 5,088,977 A | 2/1992 | Sibalis | |
| 5,121,754 A | 6/1992 | Mullett | |
| 5,433,739 A | 7/1995 | Sluijter et al. | |
| 5,529,574 A | 6/1996 | Frackelton | |
| 5,792,100 A | 8/1998 | Shantha | |
| 5,911,223 A | 6/1999 | Weaver et al. | |
| 5,938,690 A | 8/1999 | Law et al. | |
| 6,041,252 A | 3/2000 | Walker et al. | |
| 6,146,380 A | 11/2000 | Racz et al. | |
| 6,161,047 A | 12/2000 | King et al. | |
| 6,360,750 B1 | 3/2002 | Gerber et al. | |
| 6,567,702 B1 | 5/2003 | Nekhendzy et al. | |
| 6,591,138 B1 | 7/2003 | Fischell et al. | |

(Continued)

FOREIGN PATENT DOCUMENTS

| | | |
|---|---|---|
| JP | 2004-321242 | 11/2004 |
| JP | 2007-501067 | 1/2007 |

(Continued)

OTHER PUBLICATIONS

Karran September E et201 al., 1 "The Amyloid cascade hypothesis for AD," Nature Reviews Drug Discovery, vol. 10; 698-712.

(Continued)

*Primary Examiner* — Mark W. Bockelman
(74) *Attorney, Agent, or Firm* — Sughrue Mion, PLLC

(57) ABSTRACT

A method of treating hyaline cartilage of a subject is provided, the method including implanting a first exposed electrode surface in osteochondral tissue of the subject, and implanting a second exposed electrode surface in a body of the subject. Regeneration of the hyaline cartilage is promoted by activating control circuitry to drive the first and the second exposed electrode surfaces to drive nutrients toward the first exposed electrode surface. Other embodiments are also described.

20 Claims, 3 Drawing Sheets

(56) References Cited

U.S. PATENT DOCUMENTS

| | | |
|---|---|---|
| 6,602,248 B1 | 8/2003 | Sharps et al. |
| 6,620,155 B2 | 9/2003 | Underwood et al. |
| 6,832,115 B2 | 12/2004 | Borkan |
| 6,941,172 B2 | 9/2005 | Nachum |
| 6,997,941 B2 | 2/2006 | Sharkey et al. |
| 7,013,177 B1 | 3/2006 | Whitehurst et al. |
| 7,069,083 B2 | 6/2006 | Finch et al. |
| 7,120,489 B2 | 10/2006 | Shalev et al. |
| 7,155,287 B2* | 12/2006 | Gavronsky .......... A61H 39/002 607/46 |
| 7,174,221 B1 | 2/2007 | Chen et al. |
| 7,217,351 B2 | 5/2007 | Krumme |
| 7,223,227 B2 | 5/2007 | Pflueger |
| 7,270,659 B2 | 9/2007 | Ricart et al. |
| 7,317,947 B2 | 1/2008 | Wahlstrand et al. |
| 7,398,121 B2 | 7/2008 | Matsumura et al. |
| 7,509,171 B2 | 3/2009 | DiMauro |
| 7,640,062 B2 | 12/2009 | Shalev |
| 7,831,306 B2 | 11/2010 | Finch et al. |
| 7,860,569 B2 | 12/2010 | Solberg et al. |
| 8,060,207 B2 | 11/2011 | Wallace et al. |
| 8,190,248 B2 | 5/2012 | Besio et al. |
| 8,366,615 B2 | 2/2013 | Razavi |
| 8,457,761 B2 | 6/2013 | Wariar |
| 8,577,469 B2 | 11/2013 | Gross |
| 8,676,348 B2 | 3/2014 | Gross |
| 8,740,982 B2 | 6/2014 | Lee |
| 9,131,980 B2 | 9/2015 | Bloom |
| 9,616,221 B2 | 4/2017 | Gross |
| 9,724,513 B2 | 8/2017 | Lane et al. |
| 9,731,122 B2 | 8/2017 | Gross |
| 10,398,884 B2 | 9/2019 | Lad et al. |
| 10,765,527 B2 | 9/2020 | Chin et al. |
| 2002/0151948 A1 | 10/2002 | King et al. |
| 2002/0183683 A1 | 12/2002 | Lerner |
| 2003/0130707 A1 | 7/2003 | Gan et al. |
| 2003/0158589 A1 | 8/2003 | Katsnelson |
| 2003/0216792 A1 | 11/2003 | Levin et al. |
| 2003/0225331 A1 | 12/2003 | Diederich et al. |
| 2004/0002746 A1 | 1/2004 | Ryan et al. |
| 2004/0019381 A1 | 1/2004 | Pflueger |
| 2004/0049180 A1 | 3/2004 | Sharps et al. |
| 2004/0083002 A1 | 4/2004 | Belef et al. |
| 2004/0116977 A1 | 6/2004 | Finch et al. |
| 2004/0186576 A1 | 9/2004 | Biscup et al. |
| 2004/0210209 A1 | 10/2004 | Yeung et al. |
| 2005/0010205 A1 | 1/2005 | Hovda et al. |
| 2005/0021104 A1 | 1/2005 | DiLorenzo |
| 2005/0119650 A1 | 6/2005 | Sanders et al. |
| 2005/0137646 A1 | 6/2005 | Wallace et al. |
| 2005/0137647 A1 | 6/2005 | Wallace et al. |
| 2005/0159790 A1 | 7/2005 | Shalev |
| 2005/0187589 A1 | 8/2005 | Wallace et al. |
| 2005/0203599 A1 | 9/2005 | Garabedian et al. |
| 2005/0203600 A1 | 9/2005 | Wallace et al. |
| 2005/0203602 A1 | 9/2005 | Wallace et al. |
| 2005/0222647 A1 | 10/2005 | Wahlstrand et al. |
| 2005/0277996 A1 | 12/2005 | Podhajsky et al. |
| 2006/0030895 A1 | 2/2006 | Simon et al. |
| 2006/0106430 A1 | 5/2006 | Fowler et al. |
| 2006/0224223 A1 | 10/2006 | Podhajsky et al. |
| 2006/0293723 A1 | 12/2006 | Whitehurst et al. |
| 2007/0000784 A1 | 1/2007 | Paul et al. |
| 2007/0073402 A1 | 3/2007 | Vresilovic et al. |
| 2007/0162086 A1 | 7/2007 | Dilorenzo |
| 2007/0213700 A1 | 9/2007 | Davison et al. |
| 2007/0233202 A1 | 10/2007 | Wallace et al. |
| 2007/0255338 A1 | 11/2007 | Wahlstrand |
| 2007/0276201 A1 | 11/2007 | Lee et al. |
| 2008/0009927 A1 | 1/2008 | Vilims |
| 2008/0119907 A1 | 5/2008 | Stahmann |
| 2008/0177392 A1 | 7/2008 | Williams et al. |
| 2008/0260542 A1 | 10/2008 | Nishikawa et al. |
| 2009/0030399 A1 | 1/2009 | Raiszadeh |
| 2009/0062885 A1* | 3/2009 | Brighton .......... A61N 1/326 607/50 |
| 2009/0112278 A1 | 4/2009 | Wingeier et al. |
| 2009/0125080 A1 | 5/2009 | Montgomery |
| 2009/0126813 A1 | 5/2009 | Yanagisawa et al. |
| 2009/0131850 A1 | 5/2009 | Geiger |
| 2009/0216113 A1 | 8/2009 | Meier et al. |
| 2009/0312816 A1 | 12/2009 | Gross |
| 2010/0057204 A1 | 3/2010 | Kadaba et al. |
| 2010/0100185 A1 | 4/2010 | Trieu et al. |
| 2010/0131067 A1 | 5/2010 | Metcalf, Jr. et al. |
| 2010/0217369 A1 | 8/2010 | Gross |
| 2010/0324441 A1 | 12/2010 | Hargrove et al. |
| 2011/0046540 A1 | 2/2011 | Alterman et al. |
| 2011/0054518 A1 | 3/2011 | Carbunaru et al. |
| 2011/0125158 A1 | 5/2011 | Diwan et al. |
| 2011/0160638 A1 | 6/2011 | Mauge et al. |
| 2011/0160797 A1 | 6/2011 | Makous et al. |
| 2012/0041562 A1 | 2/2012 | Shachar et al. |
| 2012/0053659 A1 | 3/2012 | Molnar et al. |
| 2012/0100607 A1 | 4/2012 | Duntsch et al. |
| 2012/0191159 A1* | 7/2012 | Willeford .......... A61N 2/002 607/51 |
| 2012/0203307 A1 | 8/2012 | Schroeppel et al. |
| 2013/0066392 A1 | 3/2013 | Simon et al. |
| 2013/0102952 A1 | 4/2013 | Gross |
| 2013/0166006 A1 | 6/2013 | Williams |
| 2013/0289385 A1 | 10/2013 | Lozano et al. |
| 2013/0289599 A1 | 10/2013 | Yeung et al. |
| 2014/0058189 A1 | 2/2014 | Stubbeman |
| 2014/0088672 A1 | 3/2014 | Bedenbaugh |
| 2014/0207224 A1 | 7/2014 | Simon |
| 2014/0257168 A1 | 9/2014 | Gill |
| 2014/0324128 A1 | 10/2014 | Gross |
| 2015/0011927 A1 | 1/2015 | Hua |
| 2015/0119898 A1 | 4/2015 | Desalles et al. |
| 2016/0144164 A1 | 5/2016 | Sedighiani |
| 2016/0220699 A1 | 8/2016 | O'Heeron |
| 2016/0331970 A1 | 11/2016 | Lozano |
| 2016/0354541 A1 | 12/2016 | Crawford et al. |
| 2017/0007823 A1 | 1/2017 | Gross |
| 2017/0120053 A1 | 5/2017 | Fostick et al. |
| 2017/0274207 A1 | 9/2017 | Gross |
| 2018/0071523 A1 | 3/2018 | Gross et al. |
| 2018/0207004 A1 | 7/2018 | Yeung et al. |

FOREIGN PATENT DOCUMENTS

| | | |
|---|---|---|
| WO | 94/05369 | 3/1994 |
| WO | 01/52931 | 7/2001 |
| WO | 01/85027 | 11/2001 |
| WO | 2001/085094 | 11/2001 |
| WO | 2005/011805 | 2/2005 |
| WO | 2006/090397 | 8/2006 |
| WO | 2008/007369 | 1/2008 |
| WO | 2017/072769 | 5/2017 |

OTHER PUBLICATIONS

De La Torre JC, "Vascular Basis of Alzheimer's Pathogensis," Ann NY Acad Sci. 977:196-215 (Nov. 2002).

Weller RO et al, "Perivascular Drainage of Amyloid-b Peptides from the Brain and Its Failure in Cerebral Amyloid Angiopathy and Alzheimer's Disease," Brain Pathology 18 (Apr. 2008) 253-266.

Brief PubMed search for metal ions in Alzheimers.

An Office Action dated Sep. 27, 2016, which issued during the prosecution of U.S. Appl. No. 14/926,705.

An international Search Report and a Written Opinion both dated Aug. 7, 2008, which issued during the prosecution of Applicant's PCT/IL2007/000865.

An Office Action dated Mar. 29, 2013, which issued during the prosecution of U.S. Appl. No. 12/373,306.

An Office Action dated Oct. 31, 2011, which issued during the prosecution of U.S. Appl. No. 12/373,306.

An Office Action dated Oct. 1, 2012, which issued during the prosecution of U.S. Appl. No. 12/373,306.

(56) References Cited

OTHER PUBLICATIONS

Notice of Allowance dated Jul. 24, 2013, which issued during the prosecution of U.S. Appl. No. 12/373,306.
An Office Action dated Apr. 11, 2013, which issued during the prosecution of U.S. Appl. No. 13/663,757.
Notice of Allowance dated Oct. 28, 2013, which issued during the prosecution of U.S. Appl. No. 13/663,757.
Elixmann IM et al., "In-vitro evaluation of a drainage catheter with integrated bioimpedance electrodes to determine ventricular size," Biomed Tech 2013; 58 (Suppl. 1) Sep. 2013 (2 pages total).
An Office Action dated Aug. 31, 2015, which issued during the prosecution of U.S. Appl. No. 13/872,794.
An Applicant Initiated Interview Summary dated Dec. 14, 2015, which issued during the prosecution of U.S. Appl. No. 13/872,794.
An Office Action dated Feb. 3, 2016, which issued during the prosecution of U.S. Appl. No. 13/872,794.
Notice of Allowance dated Dec. 9, 2016, which issued during the prosecution of U.S. Appl. No. 14/794,739.
An Applicant Initiated Interview Summary dated Feb. 25, 2016, which issued during the prosecution of U.S. Appl. No. 13/872,794.
An Office Action dated Jun. 15, 2016, which issued during the prosecution of U.S. Appl. No. 13/872,794.
An International Search Report and a Written Opinion both dated Oct. 20, 2016 which issued during the prosecution of Applicant's PCT/IL2016/050728.
An Office Action dated Sep. 21, 2016, which issued during the prosecution of U.S. Appl. No. 14/794,739.
An International Search Report and a Written Opinion both dated Jan. 26, 2017 the prosecution of Applicant's PCT/IL2016/051161.
Notice of Allowance dated Jul. 14, 2017, which issued during the prosecution of U.S. Appl. No. 13/872,794.
An Office Action dated May 26, 2017, which issued during the prosecution of U.S. Appl. No. 15/433,290.
An International Preliminary Report on Patentability dated Apr. 7, 2009, which issued during the prosecution of Applicant's PCT/IL2007/000865.
Loutzenhiser, "Membrane Potential measurements in renal afferent and efferent arterioles: actions of Angiotensin II", AJP—Renal Physiol Aug. 1, 1997 vol. 273 No. 2 F307-F314.
U.S. Appl. No. 60/830,717, filed Jul. 12, 2006.
Dao-Sheng Liu et al., "Activation of Na+ and K+ Pumping Modes of (Na,K)—ATPase by an Oscillating Electric Field," The Journal of Biological Chemistry, vol. 265. No. 13, May 5, 1990. (pp. 7260-7267).
Robert F. Service.. "Electric fields deliver druas into tumors." http://news.sciencemaa.ora. Feb. 4, 2015. (5 Pages Total).
Vemengo J, "Injectable Bioadhesive Hydrogels for Nucleus Pulposus Replacement and Repair of the Damaged Intervertebral Disc: A Thesis," Drexel University (Jan. 2007).
Urban JPG et al., "The nucleus of the intervertebral disc from development to degeneration," American Zoologist 40(1): 53-61 (2000).
Cheung KMC et al., "Intervertebral disc regeneration by use of autologous mesenchymal stem cells, an experimental model in rabbits, " Abstract from the SRS 2004 Annual Meeting.
Freemont TJ et al., "Degeneration of intervertebral discs: current understanding of cellular and molecular events, and implications for novel therapies," Expert Reviews in Molecular Biology, Mar. 29, 2001 (Cambridge University Press).
An Office Action dated Sep. 12, 2011, which issued during the prosecution of U.S. Appl. No. 12/373,306.
An Office Action dated Jul. 24, 2017, which issued during the prosecution of U.S. Appl. No. 14/982,187.
An International and a Written Opinion both dated Mar. 10, 2017, which issued during the prosecution of Applicant's PCT/IL2016/051363.
An Office Action dated Mar. 25, 2019, which issued during the prosecution of U.S. Appl. No. 15/742,245.

An Office Action together with the English translation dated Aug. 19, 2020, which issued during the prosecution of Japanese Patent Application No. 2018-521586.
An Office Action dated Apr. 25, 2018, which issued during the prosecution of U.S. Appl. No. 15/637,330.
An Office Action dated Nov. 20, 2020, which issued during the prosecution of U.S. Appl. No. 16/353,407.
An Office Action dated Jan. 22, 2020, which issued during the prosecution of U.S. Appl. No. 15/771,551.
An Office Action dated Nov. 29, 2019, which issued during the prosecution of U.S. Appl. No. 15/969,411.
An International Search Report and a Written Opinion both dated May 23, 2019, which issued during the prosecution of Applicant's PCT/IL2019/050284.
An Office Action dated Jul. 29, 2019, which issued during the prosecution of U.S. Appl. No. 15/618,325.
An Office Action dated Mar. 6, 2020, which issued during the prosecution of U.S. Appl. No. 15/618,325.
Sawyer PN et al., "Measurement of streaming potentials of mammalian blood vessels, aorta and venacava, in vivo," Biophysical journal vol. 6,5 (1966): 641-51. doi:10.1016/S0006-3495(66)86683-3.
Acupuncture Injection Therapy _ Pain Arthritis Relief Center, first viewed Sep. 2020.
"Researchers developing biomaterial to treat spinal disc degeneration," Medical Press, Jun. 13, 2019 (2019-06-biomaterial-spinal-disc-degeneration).
AvistaTM MRI xx cm 8 Contact Lead Kit: Directions for Use, Boston Scientific, Apr. 2016 (91063583-01 RevC_Avista_MRI_Lead_DFU_en-USA_S).
Akbarzadeh, Abolfazl, et al. "Liposome: classification, preparation, and applications." Nanoscale research letters 8.1 (2013): 1-9.
Herrlich, Simon, et al. "Drug release mechanisms of steroid eluting rings in cardiac pacemaker lead electrodes." Engineering in Medicine and Biology Society (EMBC), 2012 Annual International Conference of the IEEE. IEEE, 2012.
Freemont, A. J., et al. "Nerve In-Growth Into Painful Intervertebral Discs is Mediated by Nerve Growth Factor Roduced by Endothelial Cells of Local Blood Vessels." Orthopaedic Proceedings. vol. 84. No. Supp_II. The British Editorial Society of Bone & Joint Surgery, 2018.
Dolor, Aaron, et al. "Matrix modification for enhancing the transport properties of the human cartilage endplate to improve disc nutrition." PloS one 14.4 (2019): e0215218.
Bowles, Robert D., and Lori A. Setton. "Biomaterials for intervertebral disc regeneration and repair." Biomaterials 129 (2017): 54-67.
Kang, James D. "Commentary on "Gene Therapy Approach for Intervertebral Disc Degeneration: An Update"." Neurospine 17.1 (2020): 15-16.
Liang, C., et al."New hypothesis of chronic back pain: low pH promotes nerve ingrowth into damaged intervertebral disks." Acta Anaesthesiologica Scandinavica 57.3 (2013): 271-277.
Lee, Ho-Jin, et al. "Effectiveness of continuous hypertonic saline infusion with an automated infusion pump for decompressive neuroplasty: a randomized clinical trial." The Korean journal of pain 32.3 (2019): 196.
An Office Action dated Feb. 16, 2021, which issued during the prosecution of U.S. Appl. No. 16/558,987.
Takeoka, Yoshiki, Takashi Yurube, and Kotaro Nishida. "Gene therapy approach for intervertebral disc degeneration: An update." Neurospine 17.1 (2020): 3.
Sobajima, S., et al. "Gene therapy for degenerative disc disease." Gene therapy 11.4 (2004): 390-401.
Sato, Kimiaki, Kensei Nagata, and Teruyuki Hirohashi. "Intradiscal pressure after repeat intradiscal injection of hypertonic saline: an experimental study." European Spine Journal 11.1 (2002): 52-56.
Meisel, Hans-Joerg, et al. "Cell therapy for treatment of intervertebral disc degeneration: a systematic review." Global spine journal 9.1_suppl (2019): 39S-52S.
A Notice of Allowance dated May 7, 2021, which issued during the prosecution of U.S. Appl. No. 16/332,606.

(56) References Cited

OTHER PUBLICATIONS

An Office Action dated Jul. 27, 2021, which issued during the prosecution of U.S. Appl. No. 17/306,209.

* cited by examiner

CARTILAGE TREATMENT

FIELD OF THE APPLICATION

The present invention relates generally to therapeutic electrical stimulation techniques, and specifically to apparatus and methods for therapeutic electrical stimulation of joints.

BACKGROUND OF THE APPLICATION

Articular cartilage is an avascular structure composed of predominantly type II collagen mixed with proteoglycans and relatively few cells. Because it lacks vascularity, articular cartilage is dependent on diffusion of nutrients and oxygen at its surface from synovial fluid.

The structure and function of articular cartilage is controlled by chondrocytes that regulate extracellular matrix (ECM) turnover and maintain tissue homeostasis. An imbalance in ECM function may lead to degenerative diseases, such as osteoarthritis.

Known cartilage repair approaches include boric marrow stimulation, such as subchondral drilling or microfracturing, and implantation of cellular or acellular scaffolds.

SUMMARY OF THE APPLICATION

In some embodiments of the present invention, a cartilage treatment system is provided for treating hyaline cartilage of a subject. The cartilage treatment system comprises a first exposed electrode surface, which is configured to be implanted in osteochondral tissue, and a second exposed electrode surface, which is configured to be implanted in the subject's body. The cartilage treatment system further comprises control circuitry that is configured to promote regeneration of the hyaline cartilage by driving the first and the second exposed electrode surfaces to drive nutrients toward the first exposed electrode surface.

The system restores the natural negative charge of the hyaline cartilage and reestablishes the natural cartilage function, thereby reviving the cartilage and reducing pain. The system may be useful for treating injuries to the cartilage, as well as osteoarthritis, which is generally characterized by damage distributed over a large portion of the cartilage. Many conventional techniques for treating cartilage are generally appropriate for treating only focal damage, such as caused by an injury, and cannot practically be used for wide-spread damage. By contrast, the system of some embodiments of the present invention is appropriate for treating osteoarthritis, because the first exposed electrode surface can be used to apply a charge to a large area of the cartilage.

There is therefore provided, in accordance with an Inventive Concept 1 of the present invention, a method of treating hyaline cartilage of a subject, the method including:

implanting a first exposed electrode surface in osteochondral tissue of the subject;

implanting a second exposed electrode surface in a body of the subject; and promoting regeneration of the hyaline cartilage by activating control circuitry to drive the first and the second exposed electrode surfaces to drive nutrients toward the first exposed electrode surface.

Inventive Concept 2. The method according to Inventive Concept 1, wherein implanting the first exposed electrode surface includes implanting the first exposed electrode surface in physical contact with an external surface of subchondral bone of the osteochondral tissue.

Inventive Concept 3. The method according to Inventive Concept 1, wherein implanting the first exposed electrode surface includes implanting the first exposed electrode surface within subchondral bone of the osteochondral tissue.

Inventive Concept 4. The method according to Inventive Concept 1, wherein implanting the first exposed electrode surface includes implanting the first exposed electrode surface within the hyaline cartilage of the osteochondral tissue.

Inventive Concept 5. The method according to Inventive Concept 1, wherein implanting the first exposed electrode surface includes implanting the first exposed electrode surface in the osteochondral tissue such that at least a portion of the first exposed electrode surface is under a chondral defect of the hyaline cartilage.

Inventive Concept 6. The method according to Inventive Concept 1, wherein implanting the first exposed electrode surface includes implanting the first exposed electrode surface in the osteochondral tissue such that at least a portion of the first exposed electrode surface is not under a chondral defect of the hyaline cartilage.

Inventive Concept 7. The method according to Inventive Concept 1, wherein the first exposed electrode surface has a surface area of 1-30 cm2.

Inventive Concept 8. The method according to Inventive Concept 1, wherein implanting the second exposed electrode surface includes implanting the second exposed electrode surface in physical contact with synovial fluid in a joint cavity of a joint capsule of the subject.

Inventive Concept 9. The method according to Inventive Concept 1, wherein implanting the second exposed electrode surface includes implanting the second exposed electrode surface in physical contact with a capsular ligament of a joint capsule of the subject.

Inventive Concept 10. The method according to Inventive Concept 1, further including implanting at least a portion of the control circuitry within the body.

Inventive Concept 11. The method according to Inventive Concept 1, wherein activating the control circuitry includes activating the control circuitry to configure the first exposed electrode surface to be a cathode and the second exposed electrode surface to be an anode.

Inventive Concept 12. The method according to Inventive Concept 1, wherein activating the control circuitry includes activating the control circuitry to drive direct current between the first and the second exposed electrode surfaces.

Inventive Concept 13. The method according to Inventive Concept 1, wherein activating the control circuitry includes activating the control circuitry to drive the first and the second exposed electrode surfaces to apply a constant current.

Inventive Concept 14. The method according to Inventive Concept 1, wherein activating the control circuitry includes activating the control circuitry to drive the first and the second exposed electrode surfaces to apply current as a series of pulses.

Inventive Concept 15. The method according to Inventive Concept 1, wherein activating the control circuitry includes activating the control circuitry to apply a voltage between the first and the second exposed electrode surfaces.

Inventive Concept 16. The method according to Inventive Concept 15, wherein the voltage is 0.1-1.1 V.

Inventive Concept 17. The method according to Inventive Concept 1, wherein activating the control circuitry includes activating the control circuitry to drive the first and the second exposed electrode surfaces to electroosmotically drive fluid containing the nutrients toward the first exposed electrode surface.

Inventive Concept 18. The method according to Inventive Concept 17, wherein activating the control circuitry includes activating the control circuitry to cyclically:

drive the first and the second exposed electrode surfaces to electroosmotically drive the nutrient-containing fluid toward the first exposed electrode surface, and provide rest periods during which the nutrient-containing fluid is not electroosmotically driven toward the first exposed electrode surface.

Inventive Concept 19. The method according to Inventive Concept 1, wherein the method further includes identifying that the subject suffers from osteoarthritis, and wherein implanting the first and the second exposed electrode surfaces includes implanting the first and the second exposed electrode surfaces responsively to identifying that the subject suffers from the osteoarthritis.

Inventive Concept 20. The method according to Inventive Concept 1, wherein implanting the first exposed electrode surface in the osteochondral tissue includes implanting a chondral implant that includes the first exposed electrode surface, the chondral implant configured to stimulate the hyaline cartilage regeneration in a chondral defect of the hyaline cartilage.

Inventive Concept 21. The method according to Inventive Concept 20, wherein implanting the second exposed electrode surface includes implanting the second exposed electrode surface at a non-zero distance from the chondral implant.

Inventive Concept 22. The method according to Inventive Concept 20, wherein the chondral implant includes one or more synthetic materials that are configured to stimulate the hyaline cartilage regeneration.

Inventive Concept 23. The method according to Inventive Concept 22, wherein the chondral implant includes a synthetic scaffold that is configured to stimulate the hyaline cartilage regeneration.

Inventive Concept 24. The method according to Inventive Concept 23, wherein the synthetic scaffold includes an electrically-conductive material that serves as the first exposed electrode surface.

Inventive Concept 25. The method according to Inventive Concept 24, wherein the electrically-conductive material includes carbon fiber.

Inventive Concept 26. The method according to Inventive Concept 25, wherein the carbon fiber is hollow carbon fiber.

Inventive Concept 27. The method according to Inventive Concept 24, wherein the electrically-conductive material includes a biocompatible bioresorbable conductive porous material.

Inventive Concept 28. The method according to Inventive Concept 24, wherein the electrically-conductive material is shaped as a thin layer.

Inventive Concept 29. The method according to Inventive Concept 23, wherein the first exposed electrode surface is coupled to the synthetic scaffold, and wherein implanting the chondral implant includes implanting the chondral implant such that the first exposed electrode surface is located deeper within the osteochondral tissue than the synthetic scaffold.

Inventive Concept 30. The method according to Inventive Concept 29, wherein the synthetic scaffold is shaped as a thin layer.

Inventive Concept 31. The method according to Inventive Concept 23, wherein the synthetic scaffold includes a layer of fibrin glue.

Inventive Concept 32. The method according to Inventive Concept 23, wherein the synthetic scaffold is biphasic.

Inventive Concept 33. The method according to Inventive Concept 20, wherein the chondral implant includes a biological tissue graft that is configured to stimulate the hyaline cartilage regeneration.

Inventive Concept 34. The method according to Inventive Concept 33, wherein the first exposed electrode surface is coupled to the biological tissue graft, and wherein implanting the chondral implant includes implanting the chondral implant such that the first exposed electrode surface is located deeper within the osteochondral tissue than the biological tissue graft.

Inventive Concept 35. The method according to Inventive Concept 20, wherein implanting the chondral implant includes implanting the chondral implant in a chondral defect of the hyaline cartilage.

Inventive Concept 36. The method according to Inventive Concept 35, wherein the chondral implant includes an osteochondral plug that is configured to stimulate the hyaline cartilage regeneration in the chondral defect.

Inventive Concept 37. The method according to Inventive Concept 36, wherein the first exposed electrode surface is located in a transition zone of the osteochondral plug between a chondral layer of the osteochondral plug and a subchondral bone layer of the osteochondral plug.

Inventive Concept 38. The method according to Inventive Concept 36, wherein the osteochondral plug includes naturally-derived cartilage.

Inventive Concept 39. The method according to Inventive Concept 36, wherein the osteochondral plug includes a biocompatible, artificial material.

There is further provided, in accordance with an Inventive Concept 40 of the present invention, apparatus for treating hyaline cartilage of a subject, the apparatus including:

a first exposed electrode surface, which is configured to be implanted in osteochondral tissue of the subject;

a second exposed electrode surface, which is configured to be implanted in a body of the subject; and control circuitry, which is configured to promote regeneration of the hyaline cartilage by driving the first and the second exposed electrode surfaces to drive nutrients toward the first exposed electrode surface.

Inventive Concept 41. The apparatus according to Inventive Concept 40, wherein the first exposed electrode surface is configured to be implanted in physical contact with an external surface of subchondral bone of the osteochondral tissue.

Inventive Concept 42. The apparatus according to Inventive Concept 40, wherein the first exposed electrode surface is configured to be implanted within subchondral bone of the osteochondral tissue.

Inventive Concept 43. The apparatus according to Inventive Concept 40, wherein the first exposed electrode surface is configured to be implanted in the hyaline cartilage of the osteochondral tissue.

Inventive Concept 44. The apparatus according to Inventive Concept 40, wherein the first exposed electrode surface has a surface area of 1-30 cm2.

Inventive Concept 45. The apparatus according to Inventive Concept 40, wherein the second exposed electrode surface is configured to be implanted in physical contact with synovial fluid in a joint cavity of a joint capsule of the subject.

Inventive Concept 46. The apparatus according to Inventive Concept 40, wherein the second exposed electrode surface is configured to be implanted in physical contact with a capsular ligament of a joint capsule of the subject.

Inventive Concept 47. The apparatus according to Inventive Concept 40, wherein at least a portion of the control circuitry is configured to be implanted within the body.

Inventive Concept 48. The apparatus according to Inventive Concept 40, wherein the control circuitry is configured to drive direct current between the first and the second exposed electrode surfaces.

Inventive Concept 49. The apparatus according to Inventive Concept 40, wherein the control circuitry is configured to drive the first and the second exposed electrode surfaces to apply a constant current.

Inventive Concept 50. The apparatus according to Inventive Concept 40, wherein the control circuitry is configured to drive the first and the second exposed electrode surfaces to apply current as a series of pulses.

Inventive Concept 51. The apparatus according to any one of Inventive Concepts 40-50, wherein the control circuitry is configured to configure the first exposed electrode surface to be a cathode and the second exposed electrode surface to be an anode.

Inventive Concept 52. The apparatus according to any one of Inventive Concepts 40-51, wherein the control circuitry is configured to apply a voltage between the first and the second exposed electrode surfaces.

Inventive Concept 53. The apparatus according to Inventive Concept 52, wherein the voltage is 0.1-1.1 V.

Inventive Concept 54. The apparatus according to any one of Inventive Concepts 40-53, wherein the control circuitry is configured to drive the first and the second exposed electrode surfaces to electroosmotically drive fluid containing the nutrients toward the first exposed electrode surface.

Inventive Concept 55. The apparatus according to Inventive Concept 54, wherein the control circuitry is configured to cyclically:
  drive the first and the second exposed electrode surfaces to electroosmotically drive the nutrient-containing fluid toward the first exposed electrode surface, and
  provide rest periods during which the nutrient-containing fluid is not electroosmotically driven toward the first exposed electrode surface.

Inventive Concept 56. The apparatus according to any one of Inventive Concepts 40-53, further including a chondral implant, which includes the first exposed electrode surface, the chondral implant configured to stimulate the hyaline cartilage regeneration in a chondral defect of the hyaline cartilage.

Inventive Concept 57. The apparatus according to Inventive Concept 56, wherein the chondral implant includes one or more synthetic materials that are configured to stimulate the hyaline cartilage regeneration.

Inventive Concept 58. The apparatus according to Inventive Concept 57, wherein the chondral implant includes a synthetic scaffold that is configured to stimulate the hyaline cartilage regeneration.

Inventive Concept 59. The apparatus according to Inventive Concept 58, wherein the synthetic scaffold includes an electrically-conductive material that serves as the first exposed electrode surface.

Inventive Concept 60. The apparatus according to Inventive Concept 59, wherein the electrically-conductive material includes carbon fiber.

Inventive Concept 61. The apparatus according to Inventive Concept 60, wherein the carbon fiber is hollow carbon fiber.

Inventive Concept 62. The apparatus according to Inventive Concept 59, wherein the electrically-conductive material includes a biocompatible bioresorbable conductive porous material.

Inventive Concept 63. The apparatus according to Inventive Concept 59, wherein the electrically-conductive material is shaped as a thin layer.

Inventive Concept 64. The apparatus according to Inventive Concept 58, wherein the first exposed electrode surface is coupled to the synthetic scaffold, and wherein the chondral implant is configured to be implanted such that the first exposed electrode surface is located deeper within the osteochondral tissue than the synthetic scaffold.

Inventive Concept 65. The apparatus according to Inventive Concept 64, wherein the synthetic scaffold is shaped as a thin layer.

Inventive Concept 66. The apparatus according to Inventive Concept 58, wherein the synthetic scaffold includes a layer of fibrin glue.

Inventive Concept 67. The apparatus according to Inventive Concept 58, wherein the synthetic scaffold is biphasic.

Inventive Concept 68. The apparatus according to Inventive Concept 56, wherein the chondral implant includes a biological tissue graft that is configured to stimulate the hyaline cartilage regeneration.

Inventive Concept 69. The apparatus according to Inventive Concept 68, wherein the first exposed electrode surface is coupled to the biological tissue graft, and the chondral implant is configured to be implanted such that the first exposed electrode surface is located deeper within the osteochondral tissue than the biological tissue graft.

Inventive Concept 70. The apparatus according to Inventive Concept 56, wherein the chondral implant is configured to be implanted in a chondral defect of the hyaline cartilage.

Inventive Concept 71. The apparatus according to Inventive Concept 70, wherein the chondral implant includes an osteochondral plug that is configured to stimulate the hyaline cartilage regeneration in the chondral defect.

Inventive Concept 72. The apparatus according to Inventive Concept 71, wherein the first exposed electrode surface is located in a transition zone of the osteochondral plug between a chondral layer of the osteochondral plug and a subchondral bone layer of the osteochondral plug.

Inventive Concept 73. The apparatus according to Inventive Concept 71, wherein the osteochondral plug includes naturally-derived cartilage.

Inventive Concept 74. The apparatus according to Inventive Concept 71, wherein the osteochondral plug includes a biocompatible, artificial material.

The present invention will be more fully understood from the following detailed description of embodiments thereof, taken together with the drawings, in which:

DETAILED DESCRIPTION OF APPLICATIONS

Figure 1:
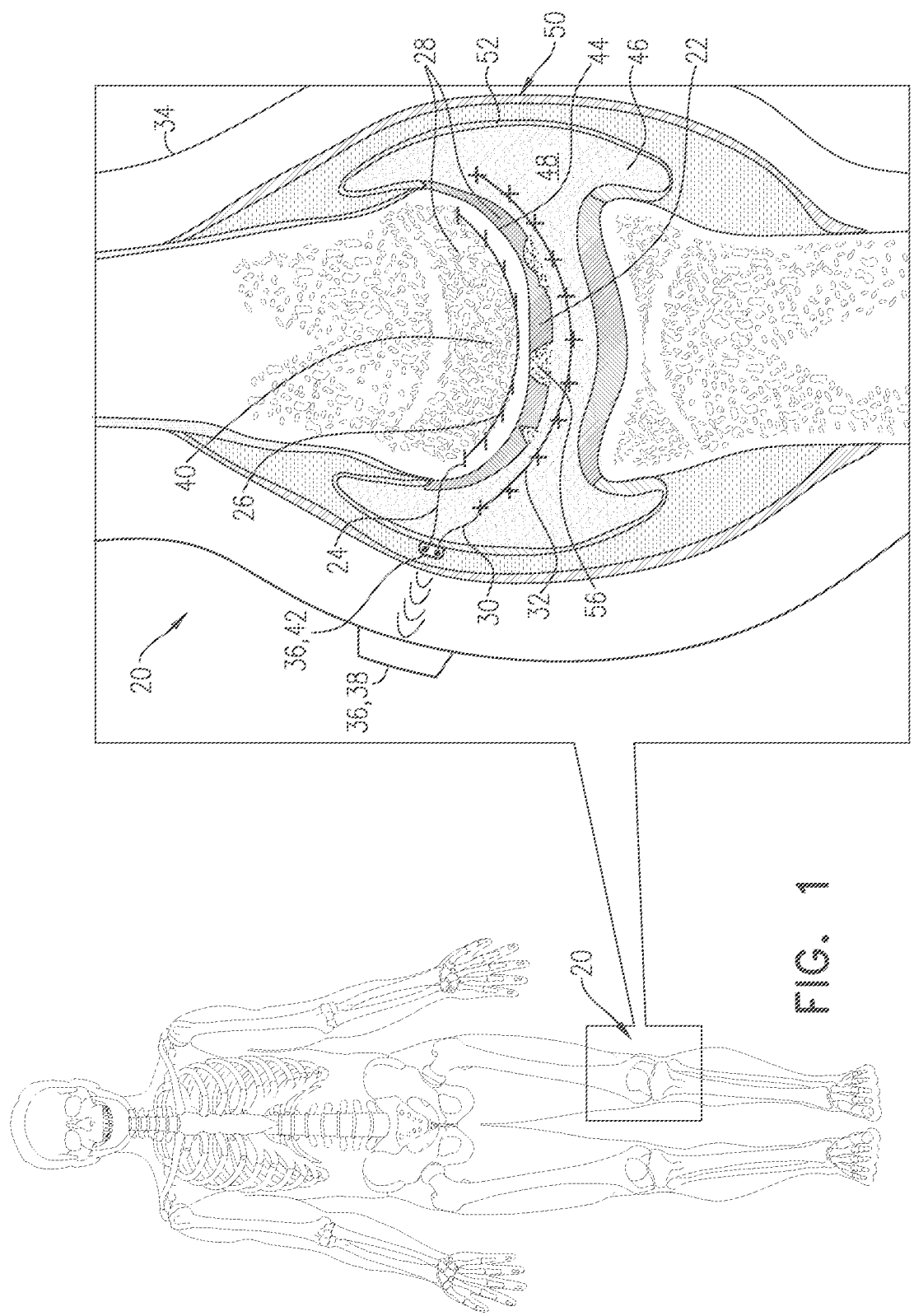
FIG. 1 is a schematic illustration of a cartilage treatment system for treating hyaline cartilage, in accordance with an application of the present invention.

FIG. 1 is a schematic illustration of a cartilage treatment system 20 for treating hyaline cartilage 22 of a subject, in accordance with an application of the present invention. Cartilage treatment system 20 comprises:

a first electrode 24, which comprises a first exposed electrode surface 26, which is configured to be implanted in osteochondral tissue 28 of the subject (osteochondral tissue 28 is composed of subchondral bone 40 and hyaline cartilage 22);

a second electrode 30, which comprises a second exposed electrode surface 32, which is configured to be implanted in a body 34 of the subject; and control circuitry 36, which is configured to promote regeneration of hyaline cartilage 22 by driving first and second exposed electrode surfaces 26 and 32 to drive nutrients toward first exposed electrode surface 26 (optionally, because of a charge of the nutrients).

As used in the present application, including in the claims, "nutrients" are substances used by cells (chondrocytes) within hyaline cartilage 22 to survive and reproduce. As used in the present application, including in the claims, oxygen is considered a nutrient, because oxygen is essential for the survival and reproduction of cells.

For some applications, first exposed electrode surface 26 is the external surface of a non-insulated portion of a wire of first electrode 24, such as shown in FIG. 1. Alternatively, first exposed electrode surface 26 comprises a separate element that is typically coupled to an insulated lead of first electrode 24.

Alternatively or additionally, for some applications, second exposed electrode surface 32 is the external surface of a non-insulated portion of a wire of second electrode 30, such as shown in FIG. 1. Alternatively, second exposed electrode surface 32 comprises a separate element that is typically coupled to an insulated lead of second electrode 30.

Typically, control circuitry 36 is configured to drive first and second exposed electrode surfaces 26 and 32 to electroosmotically drive fluid containing the nutrients toward first exposed electrode surface 26.

For some applications, first exposed electrode surface 26 is configured to be implanted:
within subchondral bone 40 of osteochondral tissue 28, such as shown in FIG. 1,
in physical contact with an external surface 44 of subchondral bone 40 (configuration not shown),
in hyaline cartilage 22 of osteochondral tissue 28 (configuration not shown), or
partially in subchondral bone 40, partially in physical contact with external surface 44 of subchondral bone 40, and partially in hyaline cartilage 22, or at two of these three sites (configurations not shown).

For some applications, first exposed electrode surface 26 has a surface area of at least 1 cm$^2$, no more than 30 cm2 (e.g., no more than 10 cm2), and/or 1-30 cm2, e.g., 1-10 cm2.

For some applications, second exposed electrode surface 32 is configured to be implanted:
in physical contact with synovial fluid 46 in a joint cavity 48 of a joint capsule 50 of the subject, such as shown in FIG. 1, and/or
in physical contact with a capsular ligament 52 of joint capsule 50 of the subject (configuration not shown).

For some applications, at least a portion of control circuitry 36 is configured to be implanted within body 34 (e.g., by injection), such as shown in FIG. 1.

For some applications, cartilage treatment system 20 comprises an implantable controller 42, which comprises at least a portion of control circuitry 36, optionally all of control circuitry 36. Optionally, control circuitry 36 does not comprise any active electronic components; for example, control circuitry 36 may comprise one or more passive diodes that are configured to rectify the current generated in the coil of control circuitry 36. Alternatively, for some applications, control circuitry 36 comprises a battery configured to be implanted in body 34.

For some applications, cartilage treatment system 20 further comprises an external unit 38, which is configured to be disposed external to body 34, such as against the skin of the body, and which is configured to wirelessly transmit power (via a coil) to a coil of implantable controller 42, and optionally to wirelessly submit control signals. Optionally, external unit 38 comprises a portion of control circuitry 36.

Figure 2:
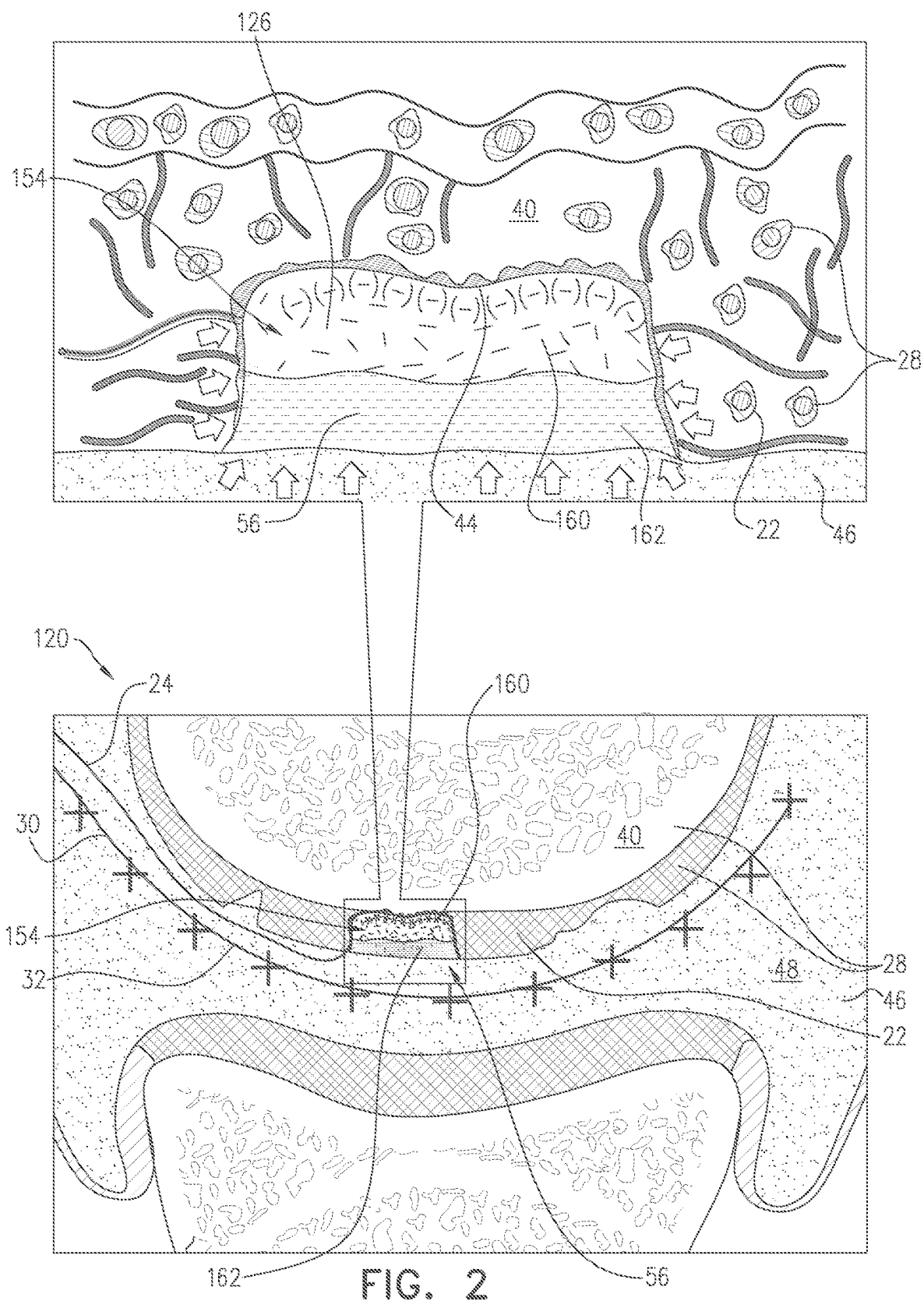
FIG. 2 is a schematic illustration of another cartilage treatment system for treating hyaline cartilage, in accordance with an application of the present invention.

Typically, control circuitry 36 is configured to configure first exposed electrode surface 26 to be a cathode and second exposed electrode surface 32 to be an anode. (The plus and minus signs in FIGS. 1 and 2 schematically illustrate the negative and positive charges of the cathode and anode, respectively.)

For some applications, control circuitry 36 is configured to apply a voltage between first and second exposed electrode surfaces 26 and 32. Typically, the voltage is at least 0.1 V, no more than 1.1 V, and/or 0.1-1.1 V).

For some applications, control circuitry 36 is configured to drive first and second exposed electrode surfaces 26 and 32 to apply a constant current.

For some applications, control circuitry 36 is configured to drive direct current between first and second exposed electrode surfaces 26 and 32. For some applications, control circuitry 36 is configured to drive the direct current as a series of pulses.

For some applications in which control circuitry 36 is configured to drive first and second exposed electrode surfaces 26 and 32 to electroosmotically drive fluid containing the nutrients toward first exposed electrode surface 26, control circuitry 36 is configured to cyclically:
drive first and second exposed electrode surfaces 26 and 32 to electroosmotically drive the nutrient-containing fluid toward first exposed electrode surface 26, and
provide rest periods during which the nutrient-containing fluid is not electroosmotically driven toward first exposed electrode surface 26.

The rest periods may allow any excess fluid driven toward first exposed electrode surface 26 to flow in the opposite direction. For example, control circuitry 36 may be configured to electroosmotically drive the nutrient-containing fluid toward first exposed electrode surface 26 for periods of time having a duration of between 3 and 10 minutes, e.g., 5 minutes, and to provide the rest periods having respective durations of between 1 and 3 minutes, e.g., 2 minutes.

Optionally, control circuitry 36 is configured to sense a voltage between first and second exposed electrode surfaces 26 and 32 during each rest period, and upon detection of a reduction to below a threshold value, again begin electroosmotically driving the nutrient-containing fluid toward first exposed electrode surface 26.

Reference is still made to FIG. 1. In an application of the present invention, a method of treating hyaline cartilage of a subject is provided, the method comprising:
implanting first exposed electrode surface 26 in osteochondral tissue 28;
implanting second exposed electrode surface 32 in body 34; and
promoting regeneration of hyaline cartilage 22 by activating control circuitry 36 to drive first and second exposed electrode surfaces 26 and 32 to drive nutrients toward first exposed electrode surface 26.

For some applications, the method further comprises identifying that the subject suffers from osteoarthritis, and first and second exposed electrode surfaces 26 and 32 are implanted responsively to identifying that the subject suffers from the osteoarthritis.

For some applications, first exposed electrode surface 26 is implanted:
within subchondral bone 40 of osteochondral tissue 28, such as shown in FIG. 1,
in physical contact with external surface 44 of subchondral bone 40 (configuration not shown),
in hyaline cartilage 22 of osteochondral tissue 28 (configuration not shown), or
partially in subchondral bone 40, partially in physical contact with external surface 44 of subchondral bone 40, and partially in hyaline cartilage 22, or at two of these three sites (configurations not shown).

For some applications, first exposed electrode surface 26 is implanted in osteochondral tissue 28 such that at least a portion of first exposed electrode surface 26 is under a chondral defect 56 of hyaline cartilage 22. Alternatively or additionally, for some applications, first exposed electrode surface 26 is implanted in osteochondral tissue 28 such that at least a portion of first exposed electrode surface 26 is not under a chondral defect 56.

For some applications, second exposed electrode surface 32 is implanted:
in physical contact with synovial fluid 46 in joint cavity 48 of joint capsule 50, and/or
in physical contact with capsular ligament 52 of joint capsule 50.

For some applications, the method further comprises implanting at least a portion of control circuitry 36 within body 34.

Reference is now made to FIG. 2, which is a schematic illustration of a portion of cartilage treatment system 120 for treating hyaline cartilage 22 of a subject, in accordance with an application of the present invention. Other than as described below, cartilage treatment system 120 is generally similar to cartilage treatment system 20 described hereinabove with reference to FIG. 1, and may implement any features thereof, mutatis mutandis. Like reference numerals refer to like parts.

Cartilage treatment system 120 further comprises a chondral implant 154, which comprises a first exposed electrode surface 126. Chondral implant 154 is configured to stimulate hyaline cartilage regeneration in a chondral defect 56 of hyaline cartilage 22. Control circuitry 36 may implement all of the features described hereinabove with reference to FIG. 1 by driving first exposed electrode surface 126 instead of first exposed electrode surface 26, mutatis mutandis.

For some applications, first exposed electrode surface 126 has a surface area of at least 1 cm2, no more than 30 cm2 (e.g., no more than 10 cm2), and/or 1-30 cm2, e.g., 1-10 cm2.

Optionally, cartilage treatment system 120 further comprises first exposed electrode surface 26, described hereinabove with reference to FIG. 1 (configuration not shown).

For some applications, chondral implant 154 comprises one or more synthetic materials that are configured to stimulate hyaline cartilage regeneration. For some of these applications, chondral implant 154 comprises a synthetic scaffold 160 that is configured to stimulate hyaline cartilage regeneration. For example, synthetic scaffold 160 may comprise an electrically-conductive material (e.g., comprising carbon fiber (e.g., a nanomaterial), such as hollow carbon fiber) that serves as first exposed electrode surface 126. For some applications, the electrically-conductive material comprises a biocompatible bioresorbable conductive porous material (e.g., arranged as a membrane). Optionally, the electrically-conductive material is shaped as a thin layer and/or as a mesh.

For some applications, first exposed electrode surface 126 is coupled to synthetic scaffold 160, and wherein chondral implant 154 is configured to be implanted such that first exposed electrode surface 126 is located deeper within osteochondral tissue 28 than synthetic scaffold 160.

For some applications, synthetic scaffold 160 is shaped as a thin layer (e.g., 0.1-2 mm thick, e.g., 1 mm thick).

For some applications, synthetic scaffold 160 comprises an outer layer of fibrin glue 162. Outer layer of fibrin glue 162 may be added to synthetic scaffold 160 during the implantation procedure, or pre-attached to the synthetic scaffold. Fibrin is permeable to nutrients, including oxygen, and thus does not interfere with the driving of the nutrients toward first exposed electrode surface 26.

For some applications, synthetic scaffold 160 is biphasic (i.e., comprises first and second regions, e.g., layers, specific for the growth of respective particular tissue types, such as cartilage and bone, respectively).

For some applications, chondral implant 154 comprises a biological tissue graft that is configured to stimulate hyaline cartilage regeneration. For example, the biological tissue graft may be autologous, e.g., implementing osteochondral allograft transplantation (OATS) or matrix-associated autologous chondrocyte implantation (MACI), as are known in the cartilage repair art.

For some of these applications, first exposed electrode surface 126 is coupled to the biological tissue graft, and chondral implant 154 is configured to be implanted such that first exposed electrode surface 126 is located deeper within osteochondral tissue 28 than the biological tissue graft.

For some applications, chondral implant 154 is configured to be implanted in chondral defect 56 of hyaline cartilage 22. For some of these applications, chondral implant 154 comprises an osteochondral plug that is configured to stimulate hyaline cartilage regeneration in chondral defect 56. Optionally, first exposed electrode surface 126 is located in a transition zone of the osteochondral plug between a chondral layer of the osteochondral plug and a subchondral bone layer of the osteochondral plug. For some applications, the osteochondral plug comprises naturally-derived cartilage. Alternatively, the osteochondral plug comprises a biocompatible, artificial material. Optionally, the osteochondral plug is cylindrical. The osteochondral plug may or may not comprise cells, as is known in the osteochondral plug art. For example, the osteochondral plug may implement techniques described in U.S. Pat. No. 6,632,246 to Simon et al.

Reference is still made to FIG. 1. In an application of the present invention, a method of treating hyaline cartilage of a subject is provided. Implanting first exposed electrode surface 26 in osteochondral tissue 28 comprises implanting chondral implant 154 that includes first exposed electrode surface 126.

For some applications, second exposed electrode surface 32 is implanted at a non-zero distance from chondral implant 154.

For some applications in which first exposed electrode surface 126 is coupled to synthetic scaffold 160, and implanting chondral implant 154 is implanted such that first exposed electrode surface 126 is located deeper within osteochondral tissue 28 than synthetic scaffold 160.

For some applications in which first exposed electrode surface 126 is coupled to the biological tissue graft, and chondral implant 154 is implanted such that first exposed electrode surface 126 is located deeper within osteochondral tissue 28 than the biological tissue graft.

For some applications, chondral implant 154 is implanted in chondral defect 56 of hyaline cartilage 22.

Figure 3:
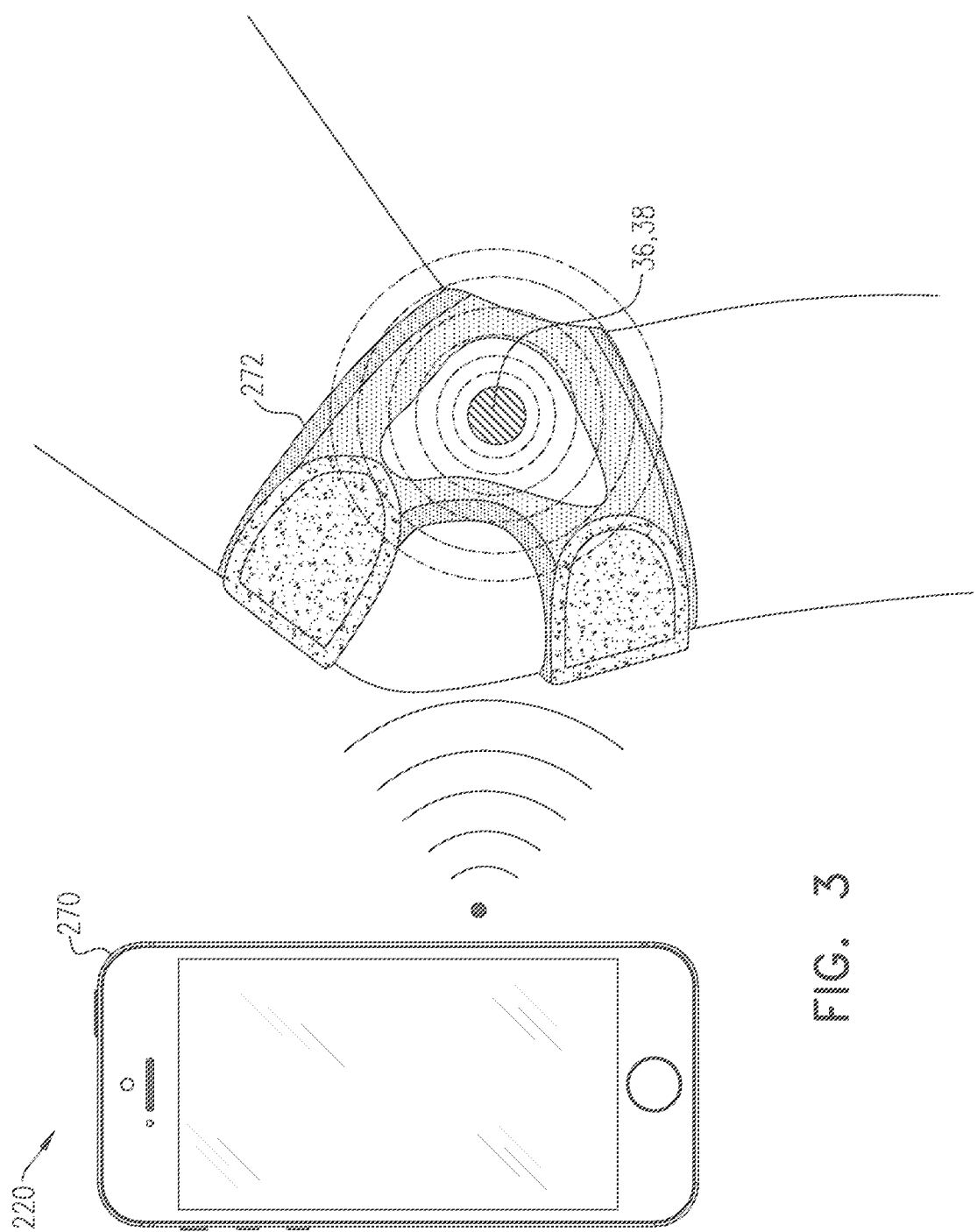
FIG. 3 is a schematic illustration of yet another cartilage treatment system for treating hyaline cartilage, in accordance with an application of the present invention.

Reference is now made to FIG. 3, which is a schematic illustration of a cartilage treatment system 220 for treating hyaline cartilage 22 of a subject, in accordance with an application of the present invention. Other than as described below, cartilage treatment system 220 is generally similar to cartilage treatment systems 20 and 120 described hereinabove with reference to FIGS. 1 and 2, respectively, and may implement any features thereof, mutatis mutandis. Like reference numerals refer to like parts. Cartilage treatment system 220 is configured to be used with a physician programmer 270, which may be implemented, for example, on a conventional smartphone, which may or may not be an element of cartilage treatment system 220. Physician programmer 270 may be used to wirelessly submit control signals to external unit 38, described hereinabove with reference to FIG. 1. For example, the control signals may include setting of personalized treatment parameters.

Optionally, cartilage treatment system 220 further comprises a knee brace 272, into which external unit 38 is incorporated.

Although cartilage treatment systems 20, 120, and 120 are illustrated as treating a knee joint, the systems may also be used to treat other synovial joints, such a hip joint, a shoulder joint, a finger joint (e.g., a knuckle joint), a toe joint, an ankle joint, an elbow joint, or a wrist. In addition, the cartilage treatment systems may be configured to treat other tissues, such as meniscus of the knee.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method of treating hyaline cartilage of a subject, the method comprising:
    implanting a first exposed electrode surface in osteochondral tissue of the subject;
    implanting a second exposed electrode surface in a body of the subject; and
    promoting regeneration of the hyaline cartilage by activating control circuitry to drive the first and the second exposed electrode surfaces to drive nutrients toward the first exposed electrode surface.

2. The method according to claim 1, wherein implanting the first exposed electrode surface comprises implanting the first exposed electrode surface in physical contact with an external surface of subchondral bone of the osteochondral tissue.

3. The method according to claim 1, wherein implanting the first exposed electrode surface comprises implanting the first exposed electrode surface within subchondral bone of the osteochondral tissue.

4. The method according to claim 1, wherein implanting the first exposed electrode surface comprises implanting the first exposed electrode surface within the hyaline cartilage of the osteochondral tissue.

5. The method according to claim 1, wherein implanting the first exposed electrode surface comprises implanting the first exposed electrode surface in the osteochondral tissue such that at least a portion of the first exposed electrode surface is under a chondral defect of the hyaline cartilage.

6. The method according to claim 1, wherein implanting the first exposed electrode surface comprises implanting the first exposed electrode surface in the osteochondral tissue such that at least a portion of the first exposed electrode surface is not under a chondral defect of the hyaline cartilage.

7. The method according to claim 1, wherein implanting the second exposed electrode surface comprises implanting the second exposed electrode surface in physical contact with synovial fluid in a joint cavity of a joint capsule of the subject.

8. The method according to claim 1, wherein implanting the second exposed electrode surface comprises implanting the second exposed electrode surface in physical contact with a capsular ligament of a joint capsule of the subject.

9. The method according to claim 1, wherein activating the control circuitry comprises activating the control circuitry to configure the first exposed electrode surface to be a cathode and the second exposed electrode surface to be an anode.

10. The method according to claim 1, wherein activating the control circuitry comprises activating the control circuitry to apply a voltage between the first and the second exposed electrode surfaces.

11. The method according to claim 10, wherein the voltage is 0.1-1.1 V.

12. The method according to claim 1, wherein activating the control circuitry comprises activating the control circuitry to drive the first and the second exposed electrode surfaces to electroosmotically drive fluid containing the nutrients toward the first exposed electrode surface.

13. The method according to claim 12, wherein activating the control circuitry comprises activating the control circuitry to cyclically:
    drive the first and the second exposed electrode surfaces to electroosmotically drive the nutrient-containing fluid toward the first exposed electrode surface, and
    provide rest periods during which the nutrient-containing fluid is not electroosmotically driven toward the first exposed electrode surface.

14. The method according to claim 1, wherein the method further comprises identifying that the subject suffers from osteoarthritis, and wherein implanting the first and the second exposed electrode surfaces comprises implanting the first and the second exposed electrode surfaces responsively to identifying that the subject suffers from the osteoarthritis.

15. The method according to claim 1, wherein implanting the first exposed electrode surface in the osteochondral tissue comprises implanting a chondral implant that includes the first exposed electrode surface, the chondral implant configured to stimulate the hyaline cartilage regeneration in a chondral defect of the hyaline cartilage.

16. The method according to claim 15, wherein implanting the second exposed electrode surface comprises implanting the second exposed electrode surface at a non-zero distance from the chondral implant.

17. The method according to claim 15, wherein the chondral implant includes a synthetic scaffold that is configured to stimulate the hyaline cartilage regeneration.

18. The method according to claim 17, wherein the synthetic scaffold includes an electrically-conductive material that serves as the first exposed electrode surface.

19. The method according to claim 17, wherein the first exposed electrode surface is coupled to the synthetic scaffold, and wherein implanting the chondral implant comprises implanting the chondral implant such that the first exposed electrode surface is located deeper within the osteochondral tissue than the synthetic scaffold.

20. The method according to claim 15, wherein implanting the chondral implant comprises implanting the chondral implant in a chondral defect of the hyaline cartilage.

\* \* \* \* \*